United States Patent [19]

Lagrange et al.

[11] Patent Number: 5,874,618

[45] Date of Patent: Feb. 23, 1999

[54] 2-NITRO-PARA-PHENYLENEDIAMINES SUBSTITUTED BY SULPHUR IN THE 5-POSITION, THE PROCESS FOR THEIR PREPARATION, DYEING COMPOSITIONS IN WHICH THEY ARE PRESENT AND THEIR USE IN THE DYEING OF KERATIN FIBERS

[75] Inventors: Alain Lagrange, Coupvray; Alain Genet, Aulnay Sous Bois, both of France

[73] Assignee: L'Oreal, Paris, France

[21] Appl. No.: 941,012

[22] Filed: Sep. 30, 1997

Related U.S. Application Data

[62] Division of Ser. No. 775,566, Dec. 31, 1996, Pat. No. 5,735,910, which is a continuation of Ser. No. 409,002, Mar. 23, 1995, abandoned.

[30] Foreign Application Priority Data

Mar. 24, 1994 [FR] France .................................. 94 03451

[51] Int. Cl.$^6$ ............................. C07C 323/36; A61K 7/13
[52] U.S. Cl. ................................. 564/305; 8/414; 8/428; 8/429; 564/341; 564/367; 564/369; 564/440
[58] Field of Search .............................. 8/414, 428, 429; 564/341, 367, 305, 369, 440

[56] References Cited

U.S. PATENT DOCUMENTS

| 4,863,482 | 9/1989 | Junino et al. .............................. 8/429 |
| 5,387,718 | 2/1995 | Kohler et al. ............................. 568/38 |

FOREIGN PATENT DOCUMENTS

| 0 203 446 | 12/1986 | European Pat. Off. . |
| 0 303 826 | 2/1989 | European Pat. Off. . |
| 0 314 162 | 5/1989 | European Pat. Off. . |
| 0 688 767 | 12/1995 | European Pat. Off. ............... 564/367 |
| 2 692 572 | 12/1993 | France . |
| 2 692 573 | 12/1993 | France . |

*Primary Examiner*—Frederick Krass
*Attorney, Agent, or Firm*—Finnegan, Henderson, Farabow, Garrett & Dunner, L.L.P.

[57] ABSTRACT

Novel nitrobenzene compounds of the nitroparaphenylenediamine type substituted by sulphur in the 5-position are disclosed. These compounds are intended especially for the dyeing of keratin fibers and in particular human hair. A process for their preparation, dyeing compositions in which these compounds are present and a dyeing process in which these compositions are used are also disclosed.

11 Claims, No Drawings

2-NITRO-PARA-PHENYLENEDIAMINES SUBSTITUTED BY SULPHUR IN THE 5-POSITION, THE PROCESS FOR THEIR PREPARATION, DYEING COMPOSITIONS IN WHICH THEY ARE PRESENT AND THEIR USE IN THE DYEING OF KERATIN FIBERS

This is a divisional application of Ser. No. 08/775,566, filed Dec. 31, 1996, now issued as U.S. Pat. No. 5,735,910, which is a continuation of Ser. No. 08/409,002, filed Mar. 23, 1995, now abandoned.

The present invention relates to novel nitrobenzene compounds of the nitroparaphenylenediamine type substituted by sulphur in the 5-position. These compounds are intended especially for the dyeing of keratin fibers and in particular for the dyeing of human hair.

There are principally two major types of hair dyeing. The first type of dyeing is semi-permanent dyeing or direct dyeing, which involves dyestuffs capable of modifying the natural coloration of the hair to a more or less pronounced degree and of resisting 4 or 5 washes with shampoo. These dyestuffs are called direct dyestuffs and are used without an oxidizing agent. The second type of dyeing is permanent dyeing or oxidative dyeing. This is carried out with so-called "oxidative" dyestuff precursors; these are colorless or weakly colored compounds which, when mixed with oxidizing products at the time of use, can produce colored dyeing compounds by an oxidative condensation process.

Direct dyestuffs are very widely used in the field of hair dyeing because they have certain advantages over the oxidative dyestuff precursors, in particular a reduction in the potential risks of allergy and the absence of hair sensitization due to the oxidative process.

The most widely used direct dyestuffs include the nitrobenzene derivatives, which on the one hand have a strong affinity for the hair and on the other hand, by virtue of the variety of possible substituents, make it possible to cover a broad range of hues from yellow through red to blue. However, the formulation of these dyestuffs presents problems on account of their resistance to washing, which is not satisfactory.

SUMMARY OF THE INVENTION

The inventors have therefore sought other nitrobenzene dyestuffs which can have a good solubility in water, in water/alcohol mixtures and more generally in the customary dyeing carriers, and which can give hair dyeings with stability to washing as well as to light, the weather and perspiration.

It is in pursuit of this research that the inventors have discovered novel 2-nitro-para-phenylenediamines substituted by sulphur in the 5-position of formula (I):

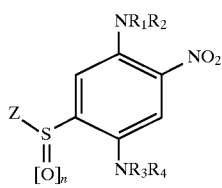

in which:
n=0, 1 or 2;
$R_1$, $R_2$, $R_3$ and $R_4$, which may be identical or different, are a hydrogen atom or a linear or branched $C_1$–$C_4$-alkyl, $C_1$–$C_4$-monohydroxyalkyl, $C_2$–$C_4$-polyhydroxyalkyl, $C_1$–$C_4$-aminoalkyl or $C_1$–$C_4$-monoalkyl or -dialkylamino-($C_1$–$C_4$)-alkyl radical; and Z is a linear or branched $C_1$–$C_4$-alkyl, $C_1$–$C_4$-monohydroxyalkyl, $C_2$–$C_4$-polyhydroxyalkyl, $C_1$–$C_4$-aminoalkyl, $C_1$–$C_4$-alkoxy-($C_1$–$C_4$)-alkyl, $C_1$–$C_4$-acetylaminoalkyl, $C_1$–$C_4$-alkylamino-($C_1$–$C_4$)-alkyl or $C_1$–$C_4$-dialkylamino-($C_1$–$C_4$)-alkyl radical, a $C_1$–$C_4$-trialkylammonium-($C_1$–$C_4$)-alkyl radical of a $C_1$–$C_4$-alkyl halide or of a $C_1$–$C_4$-alkyl sulphate (in other words, the $C_1$–$C_4$-alkyl halide or $C_1$–$C_4$-alkyl sulphate defines the counter-ion), a substituted or unsubstituted benzyl, a substituted or unsubstituted phenyl, $C_1$–$C_4$-sulphoalkyl or $C_1$–$C_4$-alkoxycarbonyl-($C_1$–$C_4$)-alkyl radical.

The alkyl, hydroxyalkyl and alkoxyalkyl radicals are preferably the methyl, ethyl, propyl, butyl, hydroxyethyl, hydroxypropyl, dihydroxypropyl and ethoxyethyl radicals.

For reasons of steric hindrance, $R_1$ is preferably a hydrogen atom.

The compounds of the formula (I) can be used in the form of the free base or in the form of a salt with acids such as hydrochloric acid, hydrobromic acid, sulphuric acid, and the like. They can therefore be in the form of the hydrochloride, hydrobromide, sulphate, and the like.

The present invention therefore relates to novel compounds of formula (I) and their cosmetically acceptable salts.

The preferred compounds of formula (I) are selected especially from the following compounds:

2-nitro-5-trimethylammonioethylthioparaphenylenediamine;

2-nitro-4-N-(β-hydroxyethyl)amino-5-[(dimethyl)aminoethyl]thioparaphenylenediamine;

2-nitro-5-(β-aminoethyl)thioparaphenylenediamine;

2-nitro-4-N-(β,γ-dihydroxypropyl)amino-5-methylthioaniline;

2-nitro-5-methylthioparaphenylenediamine;

2-nitro-5-ethylthioparaphenylenediamine;

2-nitro-5-butylthioparaphenylenediamine;

2-nitro-5-β-hydroxyethylthioparaphenylenediamine;

2-nitro-5-(β,γ-dihydroxypropyl)thioparaphenylenediamine;

1,4-N-di(β-hydroxyethyl)amino-2-nitro-5-ethoxyethylthiobenzene;

2-nitro-4-N-(β-hydroxyethyl)amino-5-β-hydroxyethylthioaniline;

2-nitro-5-(paramethoxybenzyl)thioparaphenylenediamine;

2-nitro-4-N-(β-aminoethyl)amino-5-methylthioaniline;

2-nitro-4-N-(diethylaminoethyl)amino-5-methylthioaniline;

2-nitro-4-N-(diethylaminoethyl)amino-5-ethylthioaniline;

2-nitro-4-N-(β,γ-dihydroxypropyl)amino-5-acetylaminoethylthioaniline;

2-nitro-5-acetylaminoethylthioparaphenylenediamine;

2-nitro-5-[(dimethyl)aminoethyl]thioparaphenylenediamine;

2-nitro-5-(β-aminoethyl)thioparaphenylenediamine;

2-nitro-4-amino-5-(β-hydroxypropyl)thio-N-(methyl)-aniline;

2-nitro-4-amino-5-(parahydroxyphenyl)thio-N-(methyl)-aniline;

2-nitro-5-ethoxycarbonylethylthioparaphenylenediamine;
2-nitro-5-methylsulphinylparaphenylenediamine;
2-nitro-5-mesylparaphenylenediamine;
1-N-(β-hydroxyethyl)amino-2-nitro-4-N,N-bis(β-hydroxyethyl)amino-5-isopropylthiobenzene;
2-nitro-5-sulphoethylthioparaphenylenediamine; and salts thereof.

The following may be mentioned among the more particularly preferred compounds of formula (I):
2-nitro-5-trimethylammonioethylthioparaphenylenediamine;
2-nitro-4-N-(β-hydroxyethyl)amino-5[(dimethyl)aminoethyl]thioparaphenylenediamine;
2-nitro-5-(β-aminoethyl)thioparaphenylenediamine;
2-nitro-4-N-(β,γ-dihydroxypropyl)amino-5-methylthioaniline; and salts thereof.

The present invention further relates to a process for the preparation of compounds of formula (I).

In this process, a compound of formula (II):

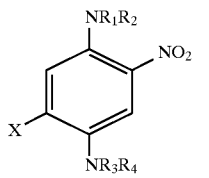

in which $R_1$, $R_2$, $R_3$ and $R_4$ are defined as indicated for the compounds of the formula (I) above, and X is a halogen atom selected from chlorine, bromine and iodine; is reacted with a thiol of the formula (III):

$$ASZ \quad (III)$$

in which Z is defined as indicated above in the formula (I), and A is a hydrogen, sodium or potassium atom; to give a compound of the formula (I) in which n=0:

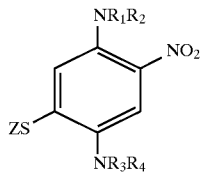

The substitution of the halogen group X is effected in a solvent such as 1,2-dimethoxyethane, dimethylformamide, N-methylpyrrolidone or dioxane. The reaction temperature may range from room temperature to the reflux temperature of the reaction medium. The hydrohalic acid "acceptors" which are preferably used are selected from sodium hydroxide, potassium hydroxide, triethylamine, sodium, potassium and calcium carbonates and the sodium salts of the thiols used.

In a second step, the compounds of formula (I) in which n is other than zero then undergo an oxidation appropriate to the value of n which it is desired to obtain. This oxidation is effected in a solvent medium in the presence of a conventional oxidizing agent for sulphur, such as a persulphate. Potassium monopersulphate may be mentioned as an example. This oxidation is preferably effected at a temperature ranging from about zero to 40° C. The compounds of formula (I) above are preferably prepared at atmospheric pressure, but they can also be prepared under pressure.

The compounds of formula (I) above can be used as dyestuffs and in particular as direct dyestuffs for the dyeing of keratin fibers, and in particular human keratin fibers such as hair. These compounds give the hair a predominantly red coloration.

The invention therefore further relates to a dyeing composition for the direct dyeing of keratin fibers, in particular human hair, in which at least one compound of the formula (I) indicated above, or one of the cosmetically acceptable salts thereof, is present in an aqueous, alcoholic or aqueous-alcoholic vehicle.

The compounds of the invention are particularly valuable for obtaining a variety of tints in association with other direct dyestuffs and especially with the conventional nitrobenzene dyestuffs.

In a preferred embodiment, the dyeing composition according to the invention contains a compound of the formula (I), or one of its cosmetically acceptable salts, in association with one or more yellow or yellow-green nitrobenzene dyestuffs and gives, on grey hair with a 90% white component, a hue ranging from 2.4 Y to 0.2 YR on the MUNSELL circle (see the publication Official Digest, April 1975, page 375, FIG. 2), the disclosure of which is incorporated herein by reference.

The inventors have found that, when using the dyestuff of the formula (I) in association with one or more conventional yellow or yellow-green dyestuffs, natural hues can be obtained which are more resistant to washing, light, the weather and perspiration than when using the dyestuffs of the prior art, especially on grey natural hair with a 90% white component or on permed grey hair.

In a more particularly preferred embodiment of the present invention, the compound of the formula (I) is associated with yellow or yellow-green dyestuffs selected from the following compounds:

1-β-hydroxyethoxy-3-methylamino-4-nitrobenzene;
1-(methylamino)-2-nitro-5-(β,γ-dihydroxypropyl)oxybenzene;
1-(β-hydroxyethylamino)-2-methoxy-4-nitrobenzene;
1-(β-aminoethylamino)-2-nitro-5-methoxybenzene;
1,3-di(β-hydroxyethylamino)-4-nitro-6-chlorobenzene;
1-amino-2-nitro-6-methylbenzene;
1-(β-hydroxyethylamino)-2-hydroxy-4-nitrobenzene;
N-(β-hydroxyethyl)-2-nitro-4-trifluoromethylaniline;
4-β-hydroxyethylamino-3-nitrobenzenesulphonic acid;
4-ethylamino-3-nitrobenzoic acid;
4-(β-hydroxyethyl)amino-3-nitrochlorobenzene;
4-(β-hydroxyethyl)amino-3-nitromethylbenzene;
4-(β,γ-dihydroxypropyl)amino-3-nitrotrifluoromethylbenzene;
1-β-ureidoethylamino-4-nitrobenzene;
O,N-bis(β-hydroxyethyl)-2-amino-5-nitrophenol;
1,3-diamino-4-nitrobenzene;
1-hydroxy-2-amino-5-nitrobenzene;
1-amino-2-[tris(hydroxymethyl)methyl]amino-5-nitrobenzene;
1-(β-hydroxyethyl)amino-2-nitrobenzene; and
4-(β-hydroxyethylamino)-3-nitrobenzamide.

The compounds of the formula (I) according to the invention can also be associated with blue nitrobenzene dyestuffs such as, for example:

1-(β-hydroxyethyl)amino-4-N,N-bis(β-hydroxyethyl)amino-2-nitrobenzene;
1-(γ-hydroxypropyl)amino-4-N,N-bis(β-hydroxyethyl)-amino-2-nitrobenzene;

1-(β-hydroxyethyl)amino-4-(N-methyl,N-β-hydroxyethyl)-amino-2-nitrobenzene;

1-(β-hydroxyethyl)amino-4-(N-ethyl,N-β-hydroxyethyl)-amino-2-nitrobenzene;

1-(β,γ-dihydroxypropyl)amino-4-(N-ethyl,N-β-hydroxyethyl)amino-2-nitrobenzene; and the 2-nitroparaphenylenediamines of formula (IV):

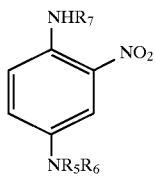
(IV)

in which:

$R_5$ is a $C_1$–$C_4$-alkyl, β-hydroxyethyl, β-hydroxypropyl or γ-hydroxypropyl radical; and $R_6$ and $R_7$, independently of one another, represent a β-hydroxyethyl, β-hydroxypropyl, γ-hydroxypropyl or β,γ-dihydroxypropyl radical; at least one of the radicals $R_5$, $R_6$ or $R_7$ being a γ-hydroxypropyl radical and it being impossible for $R_5$ and $R_6$ to be a β-hydroxyethyl radical simultaneously when $R_7$ is a γ-hydroxypropyl radical, as described in French patent application FR 92-07515, the disclosure of which is incorporated herein by reference.

The concentration of a compound of the formula (I), expressed as the free base, preferably ranges from 0.01 to 10% by weight, and more preferably ranges from 0.1 to 5% by weight, based on the total weight of the dyeing composition.

The total concentration of yellow and/or yellow-green and/or blue dyestuffs preferably ranges from about 0.05 to 3% by weight, based on the total weight of the dyeing composition.

Other nitrobenzene dyestuffs can of course be added to the associations of compounds of the formula (I) and yellow, yellow-green or blue dyestuffs according to the invention, examples being red dyestuffs selected from the following compounds:

1-hydroxy-3-nitro-4-(γ-hydroxypropylamino)benzene;

N-(β-hydroxyethyl)amino-3-nitro-4-aminobenzene;

1-amino-3-methyl-4-(β-hydroxyethyl)amino-6-nitrobenzene;

1-hydroxy-3-nitro-4-N-β-hydroxyethylaminobenzene;

1,4-diamino-2-nitrobenzene;

1-amino-2-nitro-4-methylaminobenzene;

N-(β-hydroxyethyl)-2-nitroparaphenylenediamine;

1-amino-2-nitro-4-(β-hydroxyethylamino)-5-chlorobenzene;

2-nitro-4-aminodiphenylamine; and 1-amino-3-nitro-6-hydroxybenzene.

It is also possible to add orange nitrobenzene dyestuffs selected from the following compounds:

1-(β-aminoethyl)amino-2-nitro-4-(β-hydroxyethyl)oxybenzene;

1-(β,γ-dihydroxypropyl)oxy-3-nitro-4-(β-hydroxyethyl)-aminobenzene;

1-hydroxy-3-nitro-4-aminobenzene;

1-hydroxy-2-amino-4,6-dinitrobenzene;

1-methoxy-3-nitro-4-(β-hydroxyethylamino)benzene;

2-nitro-4'-hydroxydiphenylamine; and 1-amino-2-nitro-4-hydroxy-5-methylbenzene.

It is further possible to add other direct dyestuffs such as azo dyestuffs, anthraquinone dyestuffs, dyestuffs derived from triarylmethane or basic dyestuffs, among which the dyestuffs known under the names Basic Brown 16, Basic Yellow 57, Basic Red 76 and Basic Blue 99 in the COLOR INDEX, 3rd edition, may be mentioned more particularly.

The proportion of these additional red or orange nitrobenzene dyestuffs or other direct dyestuffs can range from about 0.05 to 10% by weight, based on the total weight of the dyeing composition.

The compounds of the formula (I) can also be incorporated into dyeing compositions containing oxidative dyestuffs such as oxidative bases and couplers, so as to enrich with sheens the hues obtained with these oxidative dyestuffs.

As an appropriate vehicle, the dyeing compositions according to the invention can comprise water and/or cosmetically acceptable organic solvents, and more particularly, comprise alcohols such as ethyl alcohol, iso-propyl alcohol, benzyl alcohol and phenylethyl alcohol, or glycols or glycol ethers such as, for example, ethylene glycol and its monomethyl, monoethyl and monobutyl ethers, propylene glycol, butylene glycol, dipropylene glycol and the alkyl ethers of diethylene glycol, such as, for example, diethylene glycol monoethyl ether or monobutyl ether, in concentrations preferably ranging from 0.5 to 20% by weight, and more preferably ranging from 2 to 10% by weight, based on the total weight of the composition.

Fatty amides, such as the mono- and di-ethanolamides of acids derived from copra, lauric acid or oleic acid, can also be added to the composition according to the invention in concentrations which preferably range from 0.05 to 10% by weight.

Anionic, cationic, non-ionic, amphoteric or zwitterionic surfactants, or mixtures thereof, can also be added to the composition according to the invention. The surfactants are preferably present in the composition according to the invention in proportions which range from about 0.1 to 50% by weight, and more preferably range from about 1 to 20% by weight, based on the total weight of the composition.

Anionic surfactants, used by themselves or in a mixture, may be preferably mentioned among the surfactants, examples being the alkali metal salts, the magnesium salts, the ammonium salts, the amine salts or the alkanolamine salts of the following compounds:

alkylsulphates, alkyl-ether-sulphates, ethoxylated or non-ethoxylated alkylamidesulphates;

alkylsulphonates, alkylamidesulphonates, alphaolefin-sulfonates;

alkylsulphoacetates, alkylphosphates; and fatty acids such as lauric, myristic, oleic, ricin-oleic, palmitic and stearic acids, acids of copra oil or hydrogenated copra oil, and carboxylic acids of polyglycol ethers, the alkyl radicals of these compounds preferably having a linear chain of 12 to 18 carbon atoms.

Fatty amine salts, quaternary ammonium salts such as alkyldimethylbenzylammonium, alkyltrimethylammonium, alkyldimethylhydroxybenzylammonium and dimethylalkyl-ammonium chlorides and bromides, alkylpyridinium salts and imidazoline derivatives may be preferably mentioned as cationic surfactants. The alkyl groups of the above-mentioned quaternary ammonium derivatives are long-chain groups preferably having from 12 to 18 carbon atoms. Amine oxides may also be mentioned among these compounds of cationic character.

Alkylamino monopropionates and dipropionates, betaines such as alkylbetaines, N-alkylsulphobetaines and N-alkylamino-betaines, the alkyl radical having from 8 to 22 carbon atoms, and cycloimidinium compounds such as alkylimidazolines, may be mentioned in particular among the amphoteric surfactants which can be used.

The following may be mentioned among the non-ionic surfactants which can optionally be used in the compositions according to the invention: polyglycerolated alcohols, α-diols, alkylphenols and amides, these compounds preferably containing a $C_8$–$C_{18}$ fatty chain; polyethoxylated fatty alcohols, alkylphenols and acids, these compounds preferably containing a $C_8$ to $C_{18}$ fatty chain; condensation products of ethylene oxide and propylene oxide with fatty alcohols; polyethoxylated fatty amides preferably containing at least 5 moles of ethylene oxide; and polyethoxylated fatty amines.

The thickening products which can be added to the composition according to the invention can advantageously be selected from the group comprising sodium alginate, gum arabic, guar gum, carob gum, xanthan gum, cellulose derivatives such as methyl cellulose, hydroxyethyl cellulose, hydroxypropyl methyl cellulose and the sodium salt of carboxymethyl cellulose, and acrylic acid polymers.

It is also possible to use mineral thickeners such as bentonite. These thickeners are used by themselves or in a mixture and are preferably present in a proportion which ranges from about 0.2 to 5% by weight, based on the total weight of the composition, and more preferably ranges from about 0.5 to 3% by weight.

The dyeing composition according to the invention can be formulated at acidic, neutral or alkaline pH, it being preferable for the pH to range from 4 to 11, and more preferable for the pH to range from 5 to 10. Alkanolamines and alkali metal or ammonium hydroxides and carbonates may be mentioned among the alkalizing agents which can preferably be used. Lactic acid, acetic acid, tartaric acid, phosphoric acid, hydrochloric acid and citric acid may be mentioned among the acidifying agents which can preferably be used.

The dyeing composition according to the invention can also contain a variety of customary adjuvants such as antioxidants, perfumes, sequestering agents, film-forming products and treating agents, dispersants, hair conditioners, preservatives, opacifiers and any other adjuvant normally used in cosmetics.

The dyeing composition according to the invention can be presented in the various forms conventionally used for hair dyeing, such as thickened or gelled liquids, creams, aerosol foams or any other forms appropriate for the dyeing of keratin fibers.

The present invention further relates to a method of dyeing keratin fibers, and especially human keratin fibers such as hair, which comprises allowing the above-defined dyeing composition to act on the dry or wet keratin fibers. The composition according to the invention can be used as a no-rinse lotion, i.e. the composition according to the invention is applied to the keratin fibers, which are then dried without intermediate rinsing. In the other modes of application, the dyeing composition according to the invention is applied to the keratin fibers for a period preferably ranging from about 3 to 60 minutes, and more preferably from 5 to 45 minutes, and the fibers are rinsed, optionally washed and rinsed again, and then dried.

The following Examples are intended to illustrate the invention without however limiting its scope.

PREPARATORY EXAMPLES

Example 1

Preparation of 2-nitro-5-methylthiopara-phenylenediamine 46.9 g (0.25 mol) of 2-nitro-5-chloroparaphenylenediamine were added in portions to a suspension of 25 g (0.35 mol) of sodium thiomethylate in 350 ml of dimethoxyethane at room temperature.

The reaction was exothermic and the temperature was kept between 25° C. and 30° C. by cooling.

When the addition was complete, the mixture was stirred for half an hour and poured into 2 kg of iced water. The crystalline precipitate was filtered off, made into a paste again with water and dried.

This gave dark brown crystals (48.9 g) which melted at 168° C. (recrystallization from 96° ethanol), whose elemental analysis calculated for $C_7H_9N_3O_2S$ was:

| %          | C     | H    | N     | O     | S     |
|------------|-------|------|-------|-------|-------|
| Calculated | 42.20 | 4.55 | 21.09 | 16.06 | 16.09 |
| Found      | 42.37 | 4.59 | 21.08 | 16.08 | 16.19 |

Example 2

Preparation of 2-nitro-5-ethylthiopara-phenylenediamine

This compound was prepared by the procedure described for Example 1.

18.7 g (0.1 mol) of 2-nitro-5-chloro-para-phenylenediamine and 12.6 g (0.15 mol) of sodium thioethylate were used as the starting materials to give brick-red crystals (21.0 g) melting at 142° C. (recrystallization from ethyl acetate), whose elemental analysis calculated for $C_8H_{11}N_3O_2S$ was:

| %          | C     | H    | N     | O     | S     |
|------------|-------|------|-------|-------|-------|
| Calculated | 45.06 | 5.20 | 19.70 | 15.00 | 15.04 |
| Found      | 45.17 | 5.20 | 19.74 | 15.14 | 15.14 |

Example 3

Preparation of 2-nitro-5-butylthiopara-phenylenediamine

This compound was prepared by the procedure described for Example 1.

28.1 g (0.15 mol) of 2-nitro-5-chloroparaphenylenediamine and 24.7 g (0.22 mol) of sodium thiobutylate were used as the starting materials to give 35.7 g of red crystals melting at 129° C. (recrystallization from ethyl acetate), whose elemental analysis calculated for $C_{10}H_{15}N_3O_2S$ was:

| %          | C     | H    | N     | O     | S     |
|------------|-------|------|-------|-------|-------|
| Calculated | 49.77 | 6.27 | 17.41 | 13.26 | 13.29 |
| Found      | 49.88 | 6.32 | 17.27 | 13.40 | 13.31 |

Example 4

Preparation of 2-nitro-5-β-hydroxyethylthio-paraphenylenediamine

A suspension of 18.7 g (0.1 mol) of 2-nitro-5-chloro-paraphenylenediamine, 20.7 g (0.15 mol) of potassium carbonate and 11.7 g (0.15 mol) of 2-mercaptoethanol in 100 ml of dimethoxyethane was refluxed for one hour.

The reaction medium was poured into 600 g of iced water. The crystalline precipitate was filtered off, made into a paste again with water and dried.

This gave 22.5 g of dark garnet-red crystals which melted at 161° C. (recrystallization from 96° ethanol), whose elemental analysis calculated for $C_8H_{11}N_3O_3S$ was:

| % | C | H | N | O | S |
|---|---|---|---|---|---|
| Calculated | 41.91 | 4.84 | 18.33 | 20.94 | 13.99 |
| Found | 42.04 | 4.91 | 18.19 | 21.22 | 13.76 |

Example 5

Preparation of 2-nitro-5-(β,γ-dihydroxy-propyl) thioparaphenylenediamine

This compound was prepared by the procedure described for Example 4.

18.7 g (0.1 mol) of 2-nitro-5-chloro-para-phenylene-diamine and 16.2 g (0.15 mol) of 3-mercaptopropane-1,2-diol were used as the starting materials to give dark brown-red crystals (25.4 g) which melted at 164° C. (recrystallization from 96° ethanol), whose elemental analysis calculated for $C_9H_{13}N_3O_4S$ was:

| % | C | H | N | O | S |
|---|---|---|---|---|---|
| Calculated | 41.69 | 5.05 | 16.21 | 24.68 | 12.37 |
| Found | 41.75 | 5.10 | 46.06 | 24.91 | 12.58 |

Example 6

Preparation of 1,4-N-di(β-hydroxyethyl)amino-2-nitro-5-ethoxyethylthiobenzene

This compound was prepared by the procedure described for Example 4.

8.3 g (0.03 mol) of 1,4-N-di(β-hydroxyethyl)amino-2-nitro-5-chlorobenzene and 4.8 g (0.045 mol) of 2-ethoxyethane-thiol were used as the starting materials to give brown crystals (9.8 g) which melted at 110° C. (recrystallization from ethanol), whose elemental analysis calculated for $C_{14}H_{23}N_3O_5S$ was:

| % | C | H | N | O | S |
|---|---|---|---|---|---|
| Calculated | 48.68 | 6.71 | 12.16 | 23.16 | 9.28 |
| Found | 48.55 | 6.67 | 12.14 | 23.34 | 9.26 |

Example 7

Preparation of 2-nitro-4-N-(β-hydroxyethyl)amino-5-β-hydroxyethylthioaniline

This compound was prepared by the procedure described for Example 4.

23.1 g (0.1 mol) of 2-nitro-4-N-(β-hydroxyethyl)amino-5-chloroaniline and 11.7 g (0.15 mol) of 2-mercaptoethanol were used as the starting materials to give 21.7 g of brown-orange crystals melting at 166° C., whose elemental analysis calculated for $C_{10}H_{15}N_3O_4S$ was:

| % | C | H | N | O | S |
|---|---|---|---|---|---|
| Calculated | 43.95 | 5.53 | 15.37 | 23.42 | 11.73 |
| Found | 44.07 | 5.61 | 15.42 | 23.50 | 11.72 |

Example 8

Preparation of 2-nitro-5-(paramethoxybenzyl)-thioparaphenylenediamine

This compound was prepared by the procedure described for Example 4.

37.5 g (0.2 mol) of 2-nitro-5-chloro-para-phenylenediamine and 61.7 g (0.4 mol) of (4-methoxyphenyl) methanethiol were used as the starting materials to give, after recrystallization from 96° ethanol, dark brown crystals (34.6 g) melting at 140° C., whose elemental analysis calculated for $C_4H_{15}N_3O_3S$ was:

| % | C | H | N | O | S |
|---|---|---|---|---|---|
| Calculated | 55.07 | 4.95 | 13.76 | 15.72 | 10.50 |
| Found | 55.07 | 4.97 | 13.75 | 15.93 | 10.34 |

Example 9

Preparation of 2-nitro-4-N-(β-aminoethyl)-amino-5-methylthioaniline

This compound was prepared by the procedure described for Example 1.

46.8 g (0.2 mol) of 2-nitro-4-N-(β-aminoethyl)amino-5-chloroaniline and 25 g (0.35 mol) of sodium thiomethylate were used as the starting materials to give dark red crystals (43.4 g) melting at 153° C. (recrystallization from isopropyl acetate), whose elemental analysis calculated for $C_9H_{14}N_4O_2S$ was:

| % | C | H | N | O | S |
|---|---|---|---|---|---|
| Calculated | 44.61 | 5.82 | 23.12 | 13.21 | 13.23 |
| Found | 44.69 | 5.91 | 23.06 | 13.46 | 13.39 |

Example 10

Preparation of 2-nitro-4-N-(diethylamino-ethyl) amino-5-methylthioaniline

This compound was prepared by the procedure described for Example 1.

5.0 g (0.0174 mol) of 2-nitro-4-N-(diethylaminoethyl)-amino-5-chloroaniline and 1.9 g (0.026 mol) of sodium thiomethylate were used as the starting materials to give brown-red crystals (4.8 g) melting at 105° C. (recrystallization from isopropyl acetate), whose elemental analysis calculated for $C_{13}H_{22}N_4O_2S$ was:

| % | C | H | N | O | S |
|---|---|---|---|---|---|
| Calculated | 52.33 | 7.43 | 18.78 | 10.72 | 10.74 |
| Found | 52.56 | 7.46 | 18.81 | 10.90 | 10.66 |

Example 11

Preparation of 2-nitro-4-N-(diethylamino-ethyl) amino-5-ethylthioaniline

This compound was prepared by the procedure described for Example 1.

5.0 g (0.0174 mol) of 2-nitro-4-N-(diethylaminoethyl)-amino-5-chloroaniline and 2.2 g (0.026 mol) of sodium thioethylate were used as the starting materials to give 5.1 g of brown-red crystals melting at 61° C., whose elemental analysis calculated for $C_{14}H_{24}N_4O_2S$ was:

| % | C | H | N | O | S |
|---|---|---|---|---|---|
| Calculated | 53.82 | 7.74 | 17.93 | 10.24 | 10.26 |
| Found | 53.79 | 7.80 | 17.93 | 10.35 | 10.29 |

Example 12

Preparation of 2-nitro-4-N-(β,γ-dihydroxy-propyl) amino-5-methylthioaniline

This compound was prepared by the procedure described for Example 1.

18.3 g (0.07 mol) of 2-nitro-4-N-(β, γ-dihydroxy-propyl) amino-5-chloroaniline and 9.8 g (0.14 mol) of sodium thiomethylate were used as the starting materials to give, after purification by passage over a medium pressure column of silica gel (ethyl acetate/heptane gradient), brown-red crystals (6.2 g) melting at 133° C., whose elemental analysis calculated for $C_{10}H_{15}N_3O_4S$ was:

| % | C | H | N | O | S |
|---|---|---|---|---|---|
| Calculated | 43.95 | 5.53 | 15.37 | 23.42 | 11.73 |
| Found | 43.84 | 5.51 | 15.26 | 23.71 | 11.80 |

Example 13

Preparation of 2-nitro-4-N-(β,γ-dihydroxy-propyl) amino-5-acetylaminoethylthioaniline A suspension of 55.6 g (0.467 mol) of N-(2-mercapto-ethyl)acetamide and 15.8 g (0.24 mol) of 85% powdered potassium hydroxide in 300 ml of dimethoxyethane was heated at 45° C. until the potassium hydroxide had dissolved. 49.0 g (0.187 mol) of 2-nitro-4-N-(β, γ-dihydroxy-propyl)amino-5-chloroaniline were added in portions, the temperature being kept at 45° C.

When the addition was complete, the mixture was stirred for one hour and poured into 1 liter of iced water. The crystalline precipitate was filtered off, made into a paste again with water and recrystallized from 96° ethanol under reflux.

This gave claret-colored crystals (32.9 g) melting at 178° C., whose elemental analysis calculated for $C_{13}H_{20}N_4O_5S$ was:

| % | C | H | N | O | S |
|---|---|---|---|---|---|
| Calculated | 45.34 | 5.85 | 16.27 | 23.23 | 9.31 |
| Found | 45.38 | 5.91 | 16.24 | 22.99 | 9.27 |

Example 14

Preparation of 2-nitro-5-acetylaminoethyl-thioparaphenylenediamine

This compound was prepared by the procedure described for Example 13.

46.9 g (0.25 mol) of 2-nitro-5-chloro-paraphenylene-diamine and 74.5 g (0.625 mol) of N-(2-mercaptoethyl) acetamide were used as the starting materials to give 64.3 g of red crystals (recrystallization from 96° ethanol) melting at 162° C., whose elemental analysis calculated for $C_{10}H_{14}N_4O_3S$ was:

| % | C | H | N | O | S |
|---|---|---|---|---|---|
| Calculated | 44.43 | 5.22 | 20.73 | 17.76 | 11.86 |
| Found | 44.56 | 5.24 | 20.64 | 17.72 | 11.81 |

Example 15

Preparation of 2-nitro-5-(β-aminoethyl)-thioparaphenylenediamine dihydrochloride A solution of 20.3 g (0.075 mol) of 2-nitro-5-acetyl-aminoethylthioparaphenylenediamine, obtained in Example 14, in 65 ml of a 36% aqueous solution of hydrochloric acid was refluxed for 3 hours.

The reaction medium (yellow suspension) was cooled in an ice bath and filtered. It was made into a paste again with absolute ethanol and dried to give 8.3 g of yellow crystals melting with decomposition at 240°–243° C., whose elemental analysis calculated for $C_8H_{12}N_4O_2S \cdot 2HCl \cdot \frac{1}{2}C_2H_5OH$ was:

| % | C | H | N | O | S | Cl |
|---|---|---|---|---|---|---|
| Calculated | 33.34 | 5.28 | 17.28 | 12.34 | 9.89 | 21.87 |
| Found | 33.27 | 4.95 | 17.03 | 12.74 | 10.17 | 21.49 |

Example 16

Preparation of 2-nitro-5-[(dimethyl)amino-ethyl] thioparaphenylenediamine monohydrate The procedure described for Example 4 was used with two modifications: the solvent used was N-methyl-pyrrolidone and the reaction temperature was that of the boiling water bath (95°–100° C.).

37.5 g (0.2 mol) of 2-nitro-5-chloro-para-phenylene-diamine and 42.5 g (0.3 mol) of 2-dimethylaminoethanethiol hydrochloride were used as the starting materials to give (after recrystallization from 960 ethanol) 48.1 g of red-orange crystals melting at 122° C., whose elemental analysis calculated for $C_{10}H_{16}N_4O_2S \cdot H_2O$ was:

| % | C | H | N | O | S |
|---|---|---|---|---|---|
| Calculated | 43.78 | 6.61 | 20.42 | 17.50 | 11.69 |
| Found | 44.04 | 6.59 | 20.45 | 17.00 | 11.97 |

Example 17

Preparation of 2-nitro-4-N-(β-hydroxyethyl)amino-5-[(dimethyl)aminoethyl]thioparaphenylenediamine This compound was prepared by the procedure described for Example 16.

23.1 g (0.1 mol) of 2-nitro-4-N-(β-hydroxyethyl)amino-5-chloro-paraphenylenediamine and 21.2 g (0.15 mol) of 2-dimethylaminoethanethiol hydrochloride were used as the starting materials to give, after recrystallization from 96° ethanol, brown-red crystals (17.6 g) melting at 133° C., whose elemental analysis calculated for $C_{12}H_{20}N_4O_3S$ was:

| % | C | H | N | O | S |
|---|---|---|---|---|---|
| Calculated | 47.98 | 6.71 | 18.65 | 15.98 | 10.67 |
| Found | 48.01 | 6.77 | 18.74 | 15.94 | 10.57 |

Example 18

Preparation of 2-nitro-5-(β-aminoethyl)-thioparaphenylenediamine

This compound was prepared by the procedure described for Example 16.

18.7 g (0.1 mol) of 2-nitro-5-chloropara-phenylenediamine and 17.0 g (0.15 mol) of 2-aminoethanethiol hydrochloride were used as the starting materials to give brown-red crystals (18.0 g) melting at 149° C. (recrystallization from 96° ethanol), whose elemental analysis calculated for $C_8H_{12}N_4O_2S$ was:

| % | C | H | N | O | S |
|---|---|---|---|---|---|
| Calculated | 42.09 | 5.30 | 24.54 | 14.02 | 14.05 |
| Found | 42.20 | 5.35 | 24.31 | 14.15 | 14.17 |

Example 19

Preparation of 2-nitro-4-amino-5-(β-hydroxypropyl)thio-N-(methyl)aniline

The procedure described for the preparation of Example 4 was used.

11.5 g (0.057 mol) of 2-nitro-4-amino-5-chloro-N-(methyl)aniline and 7.8 g (0.085 mol) of 1-mercaptopropan-2-ol were used as the starting materials to give dark brown crystals (14.3 g) melting at 152° C. (recrystallization from 96° ethanol) whose elemental analysis calculated for $C_{10}H_{15}N_3O_3S$ was:

| % | C | H | N | O | S |
|---|---|---|---|---|---|
| Calculated | 46.68 | 5.88 | 16.33 | 18.65 | 12.46 |
| Found | 46.61 | 5.91 | 16.38 | 18.81 | 12.26 |

Example 20

Preparation of 2-nitro-4-amino-5-(para-hydroxyphenyl)thio-N-(methyl)aniline

This compound was prepared by the procedure described for Example 4.

11.5 g (0.057 mol) of 2-nitro-4-amino-5-chloro-N-(methyl)aniline and 11.9 g (0.085 mol) of 4-mercaptophenol were used as the starting materials to give brown-orange crystals (11.3 g) recrystallized from 96° ethanol and melting at 206° C., whose elemental analysis calculated for $C_{13}H_{13}N_3O_3S$ was:

| % | C | H | N | O | S |
|---|---|---|---|---|---|
| Calculated | 53.60 | 4.50 | 14.42 | 16.48 | 11.01 |
| Found | 53.41 | 4.58 | 14.21 | 16.95 | 10.90 |

Example 21

Preparation of 2-nitro-5-ethoxycarbonyl-ethylthioparaphenylenediamine

This compound was prepared by the procedure described for Example 16.

22.5 g (0.12 mol) of 2-nitro-5-chloropara-phenylenediamine and 25.0 g (0.186 mol) of ethylcarbonylethylthiol were used as the starting materials to give bronze-colored crystals (21.6 g) melting at 120° C., whose elemental analysis calculated for $C_{11}H_{15}N_3O_4S$ was:

| % | C | H | N | O | S |
|---|---|---|---|---|---|
| Calculated | 46.31 | 5.30 | 14.73 | 22.43 | 11.24 |
| Found | 46.31 | 5.41 | 14.66 | 22.23 | 11.41 |

Example 22

Preparation of 2-nitro-5-methylsulphinyl-paraphenylenediamine

A solution of 35.3 g (0.115 mol) of potassium monopersulphate (triple salt) in 300 ml of water was rapidly added dropwise to a suspension, cooled to 0° C., of 19.9 g (0.1 mol) of 2-nitro-5-methylthiopara-phenylenediamine (obtained in Example 1) in 300 ml of acetone, the temperature being kept at +10° C.

The mixture was stirred for one hour at +10° C., 300 g of ice were added and the reaction medium was neutralized with a dilute solution of sodium hydroxide. It was extracted with ethyl acetate and the extract was dried over sodium sulphate and evaporated to dryness under reduced pressure.

Purification by passage over a column of silica gel (heptane/ethyl acetate gradient) gave dark red crystals (7.9 g) melting at 204° C., whose elemental analysis calculated for $C_7H_9N_3O_3S$ was:

| % | C | H | N | O | S |
|---|---|---|---|---|---|
| Calculated | 39.06 | 4.21 | 19.52 | 22.30 | 14.90 |
| Found | 39.20 | 4.28 | 19.58 | 22.31 | 14.83 |

Example 23

Preparation of 2-nitro-5-mesylpara-phenylenediamine

1st step: Synthesis of 1,4-di-N-acetylamino-2-nitro-5-methylthiobenzene

A mixture of 59.7 g (0.3 mol) of 2-nitro-5-methylthioparaphenylenediamine (obtained in Example 1) and 66 ml of acetic anhydride in 350 ml of dioxane was heated for one hour in a boiling water bath.

The yellow suspension was cooled in an ice bath.

The crystalline precipitate was filtered off, washed with dioxane and then with petroleum ether and dried.

This gave yellow crystals (71.7 g) melting at 247° C., whose elemental analysis calculated for $C_{11}H_{13}N_3O_4S$ was:

| %          | C     | H    | N     | O     | S     |
| ---------- | ----- | ---- | ----- | ----- | ----- |
| Calculated | 46.64 | 4.63 | 14.83 | 22.59 | 11.32 |
| Found      | 46.68 | 4.64 | 14.89 | 22.60 | 11.14 |

2nd step:

A solution of 103 g (0.335 mol) of potassium monopersulphate (triple salt) in 700 ml of water was added rapidly at room temperature to a suspension of 38.0 g (0.134 mol) of the compound obtained above in step 1 in 700 ml of acetone, the temperature being allowed to rise to 30° C.

The mixture was stirred for 2 hours at room temperature and diluted with 700 g of iced water.

The crystalline precipitate was filtered off, made into a paste again with water and dried.

This gives yellow crystals (36.4 g) melting at 256° C. (recrystallization from acetic acid), whose elemental analysis calculated for $C_{11}H_{13}N_3O_6S$ was:

Attorney Docket No. 05725.0040

| %          | C     | H    | N     | O     | S     |
| ---------- | ----- | ---- | ----- | ----- | ----- |
| Calculated | 41.90 | 4.16 | 13.33 | 30.45 | 10.17 |
| Found      | 42.06 | 4.25 | 13.17 | 30.54 | 10.22 |

3rd step:

The compound obtained above (step 2–36.4 g) was deacetylated by heating in a boiling water bath for 30 min in a mixture of 200 ml of 36% aqueous hydrochloric acid and 40 ml of acetic acid.

The resulting mixture was cooled in an ice bath.

The crystalline hydrochloride was filtered off and taken up with 200 ml of aqueous ammonia.

The crystalline precipitate was filtered off, made into a paste again with water and dried.

This gave brown-violet crystals (12.8 g) of the expected product melting at 221° C., whose elemental analysis calculated for $C_7H_9N_3O_4S$ was:

| %          | C     | H    | N     | O     | S     |
| ---------- | ----- | ---- | ----- | ----- | ----- |
| Calculated | 36.36 | 3.92 | 18.17 | 27.68 | 13.87 |
| Found      | 36.87 | 4.01 | 18.05 | 27.52 | 13.89 |

Example 24

Preparation of 2-nitro-5-trimethylammonio-ethylthioparaphenylenediamine methylsulphate 4.8 ml (0.05 mol) of dimethyl sulphate were added to a suspension, at room temperature, of 13.7 g (0.05 mol) of 2-nitro-5-(dimethylaminoethylthio)paraphenylenediamine monohydrate, prepared in Example 16, in 250 ml of ethyl acetate.

The mixture was stirred for 4 hours at room temperature and the crystalline precipitate was filtered off and washed with ethyl acetate.

After drying, dark brown-red crystals (18.8 g) melting at 153°–154° C. were obtained, whose elemental analysis calculated for $C_{11}H_{19}N_4O_2S \cdot CH_3O_4S$ was:

| %          | C     | H    | N     | O     | S     |
| ---------- | ----- | ---- | ----- | ----- | ----- |
| Calculated | 37.69 | 5.80 | 14.65 | 25.10 | 16.77 |
| Found      | 37.72 | 5.71 | 14.52 | 24.89 | 16.98 |

Example 25

Preparation of 1-N-(β-hydroxyethyl)amino-2-nitro-4-N,N-bis(β-hydroxyethyl)amino-5-isopropyl-thiobenzene monohydrochloride 1st step: Synthesis of 1-N-(β-hydroxyethyl)amino-2-nitro-4-N,N-(di-β-hydroxyethyl)amino-5-chlorobenzene A suspension of 18.7 g (0.1 mol) of 2-nitro-5-chloro-paraphenylenediamine, 30 g of calcium carbonate and 62.5 g (0.5 mol) of 2-bromoethanol in 50 ml of water was heated for 12 hours in a boiling water bath.

Three volumes of iced water were added to the reaction medium, extraction was carried out with ethyl acetate and the extract was dried over sodium sulphate, filtered and evaporated to dryness under reduced pressure.

The orange oil obtained was purified by passage over a column of silica gel (heptane/ethyl acetate gradient).

This gave yellow-orange crystals melting at 94° C., whose elemental analysis calculated for $C_{12}H_{18}ClN_3O_5$ was:

| %          | C     | H    | Cl    | N     | O     |
| ---------- | ----- | ---- | ----- | ----- | ----- |
| Calculated | 45.08 | 5.67 | 11.09 | 13.14 | 25.02 |
| Found      | 45.11 | 5.71 | 10.83 | 13.05 | 25.02 |

2nd step:

The compound obtained above in the 1st step (9.6 g–0.03 mol) and 5.9 g (0.06 mol) of sodium thioisopropylate were reacted by the procedure described for Example 1.

After purification and conversion to the hydrochloride in absolute ethanol, this gave yellow crystals melting at 162°–164° C., whose elemental analysis calculated for $C_{15}H_{25}N_3O_5S \cdot HCl$ was:

| %          | C     | H    | N     | O     | S    | Cl   |
| ---------- | ----- | ---- | ----- | ----- | ---- | ---- |
| Calculated | 45.51 | 6.62 | 10.61 | 20.21 | 8.10 | 8.95 |
| Found      | 45.32 | 6.52 | 10.61 | 20.01 | 8.34 | 8.66 |

Example 26

Preparation of 2-nitro-5-sulphoethylthio-paraphenylenediamine monohydrate

The procedure described for Example 16 was used, the potassium carbonate being replaced with sodium carbonate.

18.7 g (0.1 mol) of 2-nitro-5-chloroparaphenylenediamine and 24.6 g (0.15 mol) of the sodium salt of 2-mercaptoethanesulphonic acid were used as the starting materials to give yellow-orange crystals (27.6 g) melting above 260° C., whose elemental analysis calculated for $C_8H_{11}N_3O_5S_2 \cdot H_2O$ was:

| %          | C     | H    | N     | O     | S     |
| ---------- | ----- | ---- | ----- | ----- | ----- |
| Calculated | 30.86 | 4.21 | 13.50 | 30.83 | 20.60 |
| Found      | 30.97 | 4.18 | 13.42 | 30.14 | 20.60 |

EXAMPLES OF DYEING COMPOSITIONS

Example 27

The following dyeing composition was prepared:

| | |
|---|---|
| 2-nitro-5-trimethylammonioethylthioparaphenylene-diamine methylsulphate | 0.25 g |
| N-(β-hydroxyethyl)amino-3-nitro-4-aminobenzene | 0.1 g |
| 1,4-di-N-(β, γ-dihydroxypropyl)aminoanthraquinone | 0.05 g |
| N-(β-hydroxyethyl)amino-2-nitroparaphenylenediamine | 0.02 g |
| propylene glycol monomethyl ether | 10 g |
| nonylphenol ethoxylated with 9 moles of ethylene oxide, sold under the name RHODIASURF NP 9 OR by RHONE POULENC | 8 g |
| copra diethanolamine sold under the name COMPERLAN KD by HENKEL | 2 g |
| citric acid q.s. | pH 9 |
| demineralized water q.s.p. | 100 g |

The above composition was applied to locks of natural grey hair with a 90% white component. It was left on the hair for 30 minutes at room temperature. After rinsing and drying, the hair was dyed an iridescent deep blond colour.

Example 28

The following dyeing composition was prepared:

| | |
|---|---|
| 2-nitro-4-N-(β-hydroxyethyl)amino-5-[(dimethyl)-aminoethyl]thioparaphenylenediamine | 0.3 g |
| 1-β-hydroxyethoxy-3-methylamino-4-nitro-benzene | 0.05 g |
| 1-hydroxy-3-nitro-4-aminobenzene | 0.03 g |
| 1-(β-aminoethylamino)-2-nitro-5-methoxy-benzene | 0.1 g |
| propylene glycol monomethyl ether | 10 g |
| nonylphenol ethoxylated with 9 moles of ethylene oxide, sold under the name RHODIASURF NP 9 OR by RHONE POULENC | 8 g |
| copra diethanolamine sold under the name COMPERLAN KD by HENKEL | 2 g |
| 2-amino-2-methylpropan-1-ol q.s. | pH 9 |
| demineralized water q.s.p. | 100 g |

The above composition was applied to locks of natural grey hair with a 90% white component. It was left on the hair for 30 minutes at room temperature. After rinsing and drying, the hair was dyed a golden coppery light blond colour.

Example 29

The following dyeing composition was prepared:

| | |
|---|---|
| 2-nitro-5-(β-aminoethyl)thioparaphenylenediamine dihydrochloride | 0.22 g |
| 1-hydroxy-3-nitro-4-(γ-hydroxypropylamino)benzene | 0.02 g |
| 4-(β-hydroxyethyl)amino-3-nitromethyl-benzene | 0.03 g |
| 1-H,N-(bis-β-hydroxyethyl)amino-3-methyl-4-N-(4'-aminophenylazo)aminobenzene | 0.05 g |
| propylene glycol monomethyl ether | 10 g |
| nonylphenol ethoxylated with 9 moles of ethylene oxide, sold under the name RHODIASURF NP 9 OR by RHONE POULENC | 8 g |
| copra diethanolamine sold under the name COMPERLAN KD by HENKEL | 2 g |
| 2-amino-2-methylpropan-1-ol q.s. | pH 9 |
| demineralized water q.s.p. | 100 g |

The above composition was applied to locks of natural grey hair with a 90% white component. It was left on the hair for 30 minutes at room temperature. After rinsing and drying, the hair was dyed an iridescent coppery blond colour.

Example 30

The following dyeing composition was prepared:

| | |
|---|---|
| 2-nitro-4-N-(β,γ-dihydroxypropyl)amino-5-methylthioaniline | 0.15 g |
| 1-N-(β-hydroxyethyl)amino-4-(N-ethyl,N-β-hydroxyethyl)amino-2-nitrobenzene | 0.1 g |
| 1-(β-aminoethyl)amino-2-nitro-4-(β-hydroxyethyl)oxybenzene | 0.07 g |
| propylene glycol monomethyl ether | 10 g |
| nonylphenol ethoxylated with 9 moles of ethylene oxide, sold under the name RHODIASURF NP 9 OR by RHONE POULENC | 8 g |
| copra diethanolamine sold under the name COMPERLAN KD by HENKEL | 2 g |
| citric acid q.s. | pH 9 |
| demineralized water q.s.p. | 100 g |

The above composition was applied to locks of natural grey hair with a 90% white component. It was left on the hair for 30 minutes at room temperature. After rinsing and drying, the hair was dyed an iridescent coppery light blond colour.

What is claimed is:

1. A 2-nitroparaphenylenediamine compound substituted by sulphur in the 5-position of formula (I):

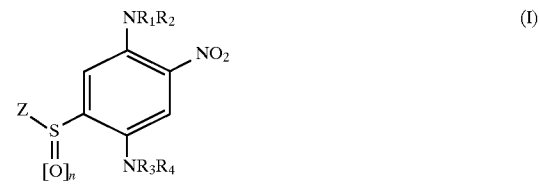

in which:

n=0, 1 or 2;

$R_1$, $R_2$, $R_3$ and $R_4$, which may be identical or different, are a hydrogen atom or a linear or branched $C_1$–$C_4$-alkyl, a linear or branched $C_1$–$C_4$-monohydroxyalkyl, a linear or branched $C_2$–$C_4$-polyhydroxyalkyl, a linear or branched $C_1$–$C_4$-aminoalkyl, a linear or branched $C_1$–$C_4$-monoalkyl-amino-($C_1$–$C_4$)-alkyl radical, or a linear or branched $C_1$–$C4$-dialkyl-amino-($C_1$–$C_4$)-alkyl radical; and Z is a linear or branched $C_1$–$C_4$-alkyl, a linear or branched $C_1$–$C_4$-monohydroxyalkyl, a linear or branched $C_2$–$C_4$-polyhydroxyalkyl, a linear or branched $C_1$–$C_4$-aminoalkyl, a linear or branched $C_1$–$C_4$-alkoxy-($C_1$–$C_4$)-alkyl, a linear or branched $C_1$–$C_4$-acetylaminoalkyl, a linear or branched $C_1$–$C_4$-monoalkylamino-($C_1$–$C_4$)-alkyl or a linear or branched $C_1$–$C_4$-dialkylamino-($C_1$–$C_4$)-alkyl radical, a linear or branched $C_1$–$C_4$-trialkylammonio-($C_1$–$C_4$)-alkyl radical of a $C_1$–$C_4$-alkyl halide or of a $C_1$–$C_4$-alkyl sulphate, a benzyl, a phenyl, a linear or branched $C_1$–$C_4$-sulphoalkyl or a linear or branched $C_1$–$C_4$-alkoxycarbonyl-($C_1$–$C_4$)-alkyl radical; or a cosmetically acceptable salt thereof.

2. A compound according to claim 1, wherein the alkyl, hydroxyalkyl or alkoxyalkyl radicals are selected from methyl, ethyl, propyl, butyl, hydroxyethyl, hydroxypropyl, dihydroxypropyl or ethoxyethyl.

3. A compound according to claim 1, wherein $R_1$ is a hydrogen atom.

4. A compound according to claim 1, which is selected from the following compounds:

2-nitro-5-trimethylammonioethylthioparaphenylenediamine;
2-nitro-4-N-(β-hydroxyethyl)amino-5[(dimethyl)aminoethyl]thioparaphenylenediamine;
2-nitro-5-(β-aminoethyl)thioparaphenylenediamine;
2-nitro-4-N-(β,γ-dihydroxypropyl)amino-5-methylthioaniline;
2-nitro-5-methylthioparaphenylenediamine;
2-nitro-5-ethylthioparaphenylenediamine;
2-nitro-5-butylthioparaphenylenediamine;
2-nitro-5-β-hydroxyethylthiopara-phenylenediamine;
2-nitro-5-(β,γ-dihydroxypropyl)thioparaphenylenediamine;
1,4-N-di(β-hydroxyethyl)amino-2-nitro-5-ethoxyethylthiobenzene;
2-nitro-4N-(β-hydroxyethyl)amino-5-β-hydroxyethylthioaniline;
2-nitro-5-(paramethoxybenzyl)thioparaphenylenediamine;
2-nitro-4-N-(β-aminoethyl)amino-5-methylthioaniline;
2-nitro-4-N-(diethylaminoethyl)amino-5-methylthioaniline;
2-nitro-4-N-(diethylaminoethyl)amino-5-ethylthioaniline;
2-nitro-4-N-(β,γ-dihydroxypropyl)amino-5-acetylaminoethylthioaniline;
2-nitro-5-acetylaminoethylthioparaphenylenediamine;
2-nitro-5-[(dimethyl)aminoethyl]thioparaphenylenediamine;
2-nitro-5-(β-aminoethyl)thioparaphenylenediamine;
2-nitro-4-amino-5-(β-hydroxypropyl)thio-N(methyl)aniline;
2-nitro-4-amino-5-(parahydroxyphenyl)thio-N(methyl)aniline;
2-nitro-5-ethoxycarbonylethylthioparaphenylenediamine;
2-nitro-5-methylsulphinylparaphenylenediamine;
2-nitro-5-mesylparaphenylenediamine;
1-N-(β-hydroxyethyl)amino-2-nitro-4-N,N-bis(β-hydroxyethyl)amino-5-isopropylthiobenzene;
2-nitro-5-sulphoethylthioparaphenylenediamine; or a cosmetically acceptable salt thereof.

5. A process for the preparation of a compound of formula (I) according to claim 1, which comprises:
reacting a compound of the formula (II):

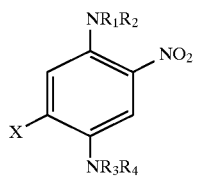

(II)

in which $R_1$, $R_2$, $R_3$ and $R_4$, which may be identical or different, are a hydrogen atom or a linear or branched $C_1$–$C_4$-alkyl, a linear or branched $C_1$–$C_4$-monohydroxyalkyl, a linear or branched $C_2$–$C_4$-polyhydroxyalkyl, a linear or branched $C_1$–$C_4$-aminoalkyl, a linear or branched $C_1$–$C_4$-monoalkylamino-($C_1$–$C_4$)-alkyl radical, or a linear or branched $C_1$–$C_4$-dialkyl-amino-($C_1$–$C_4$)-alkyl radical, and X is a halogen atom selected from chlorine, bromine or iodine;

with a thiol of the formula (III):

in which Z is a linear or branched $C_1$–$C_4$-alkyl, a linear or branched $C_1$–$C_4$-monohydroxyalkyl, a linear or branched $C_2$–$C_4$-polyhydroxyalkyl, a linear or branched $C_1$–$C_4$-aminoalkyl, a linear or branched $C_1$–$C_4$-alkoxy-($C_1$–$C_4$)-alkyl, a linear or branched $C_1$–$C_4$-acetylaminoalkyl, a linear or branched $C_1$–$C_4$-monoalkylamino-($C_1$–$C_4$)-alkyl or a linear or branched $C_1$–$C_4$-dialkylamino-($C_{1-4}$)-alkyl radical, a linear or branched $C_1$–$C_4$-trialkylammonio-($C_1$–$C_4$)-alkyl radical of a $C_1$–$C_4$-alkyl halide or of a $C_1$–$C_4$-alkyl sulphate, a benzyl, a phenyl, a linear or branched $C_1$–$C_4$,sulphoalkyl or a linear or branched $C_1$–$C_4$-alkoxycarbonyl-($C_1$–$C_4$)-alkyl radical, or a cosmetically acceptable salt thereof, and A is a hydrogen, sodium or potassium atom; wherein said reacting occurs in a solvent medium, at a temperature ranging from room temperature to the reflux temperature of the reaction medium, and in the presence of a hydrohalic acid acceptor, to give a compound of the formula (I) in which n=0:

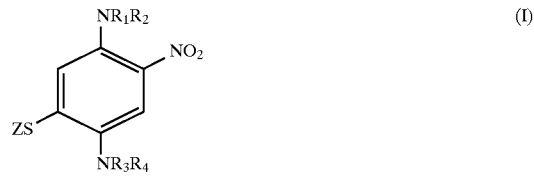

(I)

6. A process according to claim 5, which further comprises oxidizing a compound of formula (I) in which n=0, wherein said oxidizing occurs in a solvent medium, in the presence of an oxidizing agent for sulphur, and at a temperature ranging from zero to 40° C., to give a compound of the formula (I) in which n=1 or 2.

7. A process according to claim 6, wherein said oxidizing agent for sulphur is potassium monopersulphate.

8. A process according to claim 5, wherein said solvent is selected from 1,2-dimethoxyethane, dimethylformamide, N-methylpyrrolidone or dioxane.

9. A process according to claim 6, wherein said solvent is selected from 1,2-dimethoxyethane, dimethylformamide, N-methylpyrrolidone or dioxane.

10. A process according to claim 5, wherein said hydrohalic acid acceptor is selected from sodium hydroxide, potassium hydroxide, triethylamine, sodium carbonate, potassium carbonate, calcium carbonate, or the salts of the thiol of formula (III) which was used.

11. A process according to claim 8, wherein said hydrohalic acid acceptor is selected from sodium hydroxide, potassium hydroxide, triethylamine, sodium carbonate, potassium carbonate, calcium carbonate, or the salts of the thiol of formula (III).

* * * * *

UNITED STATES PATENT AND TRADEMARK OFFICE
CERTIFICATE OF CORRECTION

PATENT NO. : 5,874,618
DATED : February 23, 1999
INVENTOR(S) : Alain LE GRANGE et al.

It is certified that error appears in the above-identified patent and that said Letters Patent is hereby corrected as shown below:

IN THE CLAIMS:

Claim 1, col. 18, line 55, change "C4" to --$C_4$--.

Claim 4, col. 19, line 27, change "4N" to --4-N--.

Signed and Sealed this

Twenty-ninth Day of June, 1999

Attest:

Q. TODD DICKINSON

*Attesting Officer*       *Acting Commissioner of Patents and Trademarks*